United States Patent [19]

Berges

[11] 4,060,610

[45] Nov. 29, 1977

[54] PHARMACEUTICAL COMPOSITIONS COMPRISING 7-ACYL-3-(SUBSTITUTED TRIAZOLYL THIOMETHYL)-CEPHALOSPORINS AND METHODS OF TREATING BACTERIAL INFECTIONS

[75] Inventor: David A. Berges, Wayne, Pa.

[73] Assignee: SmithKline Corporation, Phila., Pa.

[21] Appl. No.: 731,401

[22] Filed: Oct. 12, 1976

Related U.S. Application Data

[62] Division of Ser. No. 536,759, Dec. 27, 1974, Pat. No. 3,989,694.

[51] Int. Cl.$^2$ ............................................. A61K 31/545
[52] U.S. Cl. .................................................. 424/246
[58] Field of Search ......................................... 424/246

[56] References Cited

U.S. PATENT DOCUMENTS

| 3,759,904 | 9/1973 | Crast, Jr. ........................ 260/243 C |
| 3,796,801 | 3/1974 | Guavini ............................. 424/246 |
| 3,813,388 | 5/1974 | Crast, Jr. ........................ 260/239.1 |

FOREIGN PATENT DOCUMENTS

| 814,546 | 11/1975 | Belgium. |
| 6,916,151 | 4/1971 | Netherlands. |

*Primary Examiner*—Jerome D. Goldberg
*Attorney, Agent, or Firm*—Janice E. Williams; William H. Edgerton; Alan D. Lourie

[57] ABSTRACT

The compounds of this invention are cephalosporins having various acyl substituents at the 7-position and a substituted triazolyl thiomethyl group at the 3-position of the cephem nucleus and intermediates for the preparation thereof. The 7-acylated compounds have antibacterial activity.

20 Claims, No Drawings

PHARMACEUTICAL COMPOSITIONS COMPRISING 7-ACYL-3-(SUBSTITUTED TRIAZOLYL THIOMETHYL)-CEPHALOSPORINS AND METHODS OF TREATING BACTERIAL INFECTIONS

This is a division of application Ser. No. 536,759, filed Dec. 27, 1974, now U.S. Pat. No. 3,989,694.

This invention relates to a new series of cephalosporin compounds which have antibacterial activity when administered orally or parenterally and to intermediates for the preparation thereof. In particular, the biologically active cephalosporin compounds of this invention have a substituted triazolyl thiomethyl group at the 3-position of the cephem nucleus.

The compounds of this invention are represented by the following structural formula:

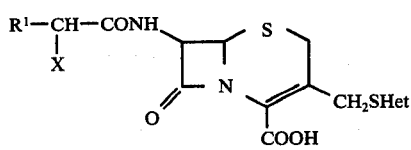

Formula I in which:
R$^1$ is thienyl, phenyl or phenyl substituted with one or two groups selected from hydroxy, halo, nitro, hydroxymethyl, amino, lower alkylamino, di(lower)alkylamino, formamido, or carboxymethylamino;

X is amino or hydroxy; and

Het is 1,2,4-triazolyl or 1,2,3,-triazolyl each of which is substituted with —(CHR$^2$)$_n$COR$^3$, where R$^2$ is hydrogen or lower alkyl, $n$ is zero to six and R$^3$ is hydroxy, lower alkoxy, amino, lower alkylamino or di(lower)alkylamino, or a non-toxic pharmaceutically acceptable salt thereof.

As used herein, the terms "lower alkyl" and "lower alkoxy" refer to groups having from one to four carbon atoms; "halo" refers to fluoro, chloro and bromo.

Preferred compounds of this invention are represented by Formula I where R$^1$ is thienyl, phenyl or phenyl substituted with one or two groups selected from hydroxy, halo, nitro, hydroxymethyl, amino, lower alkylamino, di(lower)alkylamino, formamido, ureido or carboxymethylamino; X is amino or hydroxy; Het is 1,2,3-triazol-5-yl or 1,2,4-triazol-3-yl each of which is substituted with —(CHR$^2$)$_n$COR$^3$, where R$^2$ is hydrogen, $n$ is zero to four and R$^3$ is hydroxy, lower alkoxy, amino, lower alkylamino or di(lower)alkylamino.

Advantageous compounds of this invention are represented by Formula I where R$^1$ is phenyl or hydroxyphenyl; X is amino or hydroxy; Het is 1,2,3-triazol-5-yl or 1,2,4-triazol-3-yl each of which is substituted with —(CHR$^2$)$_n$COR$^3$, where R$^2$ is hydrogen, $n$ is zero to four and R$^3$ is hydroxy, lower alkoxy, amino, lower alkylamino or di(lower)alkylamino.

Most advantageous are the compounds represented by Formula I where R$^1$ is phenyl or 4-hydroxyphenyl; X is amino or hydroxy; Het is 1,2,3-triazol-5-yl or 1,2,4-triazol-3-yl each of which is substituted with —(CHR$^2$)$_n$COR$^3$, where R$^2$ is hydrogen, $n$ is zero to four and R$^3$ is hydroxy, lower alkoxy or amino.

Particularly preferred are the compounds 7-D-mandelamido-3-(5-carboxymethyl-1,2,4-triazol-3-ylthiomethyl)-3-cephem-4-carboxylic acid, 7-(D-α-amino-phenylacetamido)-3-(5-carboxymethyl-1,2,4-triazol-3-ylthiomethyl)-3-cephem-4-carboxylic acid, 7-(D-α-amino-4-hydroxyphenylacetamido)-3-(5-carboxymethyl-1,2,4-triazol-3-ylthiomethyl)-3-cephem-4-carboxylic acid and 7-(D-α-amino-4-hydroxyphenylacetamido)-3-(4-carbamoyl-1,2,3-triazol-5-ylthiomethyl)-3-cephem-4-carboxylic acid.

Cephalosporin derivatives having a substituted α-aminophenylacetamido, substituted mandelamido or α-amino- or α-hydroxythienylacetamido group at the 7-position are well documented in the prior art. Substitution by a substituted S-heterocyclicthiomethyl group at the 3-position of the cephem nucleus is also known and is disclosed in Netherlands Pat. No. 6,916,151 where Het is, among others, triazolyl substituted with, inter alia, carboxy, carbalkoxy, alkoxyalkylaminocarbonyl and dialkylaminoalkylaminocarbonyl. These cephalosporins, however, have a similarly substituted heterocyclic acetamido group at the 7-position. No compounds containing both a 7-substituted α-aminophenylacetamido, 7-substituted mandelamido or 7-(α-amino- or α-hydroxy)-thienylacetamido group and the 3-substituted triazolylthiomethyl moiety disclosed herein are believed to be known to the art.

The compounds of Formula I are prepared by acylation of an appropriate 7-amino-3-substituted triazolyl-thiomethyl cephalosporin nucleus of Formula II:

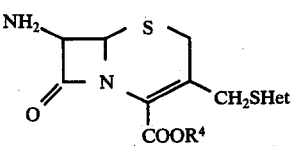

Formula II in which:
Het is 1,2,4-triazolyl or 1,2,3-triazolyl each of which is substituted with —(CHR$^2$)$_n$COR$^3$, where R$^2$ is hydrogen or lower alkyl, $n$ is zero to six and R$^3$ is hydroxy, lower alkoxy, amino, lower alkylamino or di(lower)alkylamino; and R$^4$ is hydrogen or a protecting ester group, with an appropriately substituted phenyl or thienyl acetic acid followed by removal of the protective groups. The carboxylic acid group is activated by any of the standard methods such as conversion to the mixed anhydride, acid chloride or activated ester. In addition, a reagent such as dicyclohexylcarbodiimide or carbonyldiimidazole can be used provided that the carboxyl group on the cephem nucleus is protected with an easily removable protecting group such as a benzhydryl, t-butyl, trichloroethyl, benzyl, benzyloxymethyl, p-nitrophenyl, p-methoxyphenyl, p-methoxybenzyl or p-nitrobenzyl ester. When X is amino, the α-amino group of the phenyl or thienyl acebic acid moiety is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides. The compounds represented by Formula II above are also considered as objects of this invention.

Alternatively, the compounds of Formula I are prepared by acylating 7-aminocephalosporanic acid with an appropriately substituted and protected, as described above, phenyl or thienyl acetic acid and then displacing the 3-acetoxy group with the desired substituted triazole thiol with subsequent removal of the protective group(s).

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyreneamine ion exchange resin (Amberlite IR-45) or else by basification of an aqueous solution of the salt.

The substituted phenyl or thienyl acetic acid starting materials are known or are prepared by known methods, for example as described in Belgian Pat. No. 774,029 in the case of substituted phenyl glycines and in U.S. Pat. Nos. 3,422,099 and 3,352,858 for substituted thienyl acetic acids. Examples of substituted mandelic acids are found in U.S. Pat. No. 3,641,021.

The 7-amino-3-substituted triazolylthiomethyl cephalosporin starting materials of Formula II are prepared from reaction of 7-aminocephalosporanic acid and a substituted triazole thiol.

The substituted 1,2,3-triazole thiols not known to the art are prepared by rearrangement of a correspondingly substituted amino thiadiazole according to the procedure of Goerdeler and Gnad [*Chem. Ber.* 99:1618 (1966)], by conversion of a suitably substituted hydroxy 1,2,3-triazole to the corresponding thiol by the method of Hoover and Day [*J. Amer. Chem. Soc.* 78:5832 (1956)] or by reaction of an acetylene carboxylic acid with a substituted azide and subsequent decarboxylation and thiation.

The compounds of this invention are capable of forming salts with, for example, the alkali metals such as sodium or potassium, the alkaline earth metals such as calcium or with the ammonium cation. When X is amino, the compounds can exist as the zwitterion or as an acid or base salt. These salts are prepared by standard methods using a wide variety of nontoxic pharmaceutically acceptable acids and bases known in the art and are also considered as objects of this invention.

It will be recognized that because of the asymmetric α-carbon atom in the 7-acetamido group of Formula I, optical isomers will exist. Racemic or resolved products are obtained depending upon whether a racemic or resolved side chain acid is used as an acylating agent. The resolved side chain acids are readily obtained from the racemic compounds by resolution according to well known methods including fractional crystallization of a salt formed with an optically active acid or base. All of the isomers, including separated isomers and mixtures thereof, are included within the scope of this invention.

The compounds of Formula I have antibacterial activity against both Gram-positive and Gram-negative organisms. Minimum inhibitory concentrations (MIC's) ranged from 0.2 to > 200 μg./ml. in in vitro testing. These results are shown in Table I below for representative compounds of this invention. In vivo mouse protection data are given in Table 2. Compound numbers corresponding to structures are given in the experimental section.

TABLE 1

| Bacteria | MIC in vitro (μg./ml.) | | | | | | | | |
|---|---|---|---|---|---|---|---|---|---|
| | I | II | III | IV | V | VI | VII | VIII | IX |
| S. aureus HH 127 | 12.5,6 | 6 | 6 | 3 | 12.5 | 6.3 | 12.5 | 12.5 | 3.1 |
| S. aureus SK 23390 | 25, 13 | 6 | 6 | 3 | 12.5, 19 | 3.1 | 12.5 | 25 | 1.6 |
| S. villaluz | 200 | 100 | 100 | 50 | 200 | 200 | >200 | 200 | 200 |
| Strep. faecalis HH 34358 | 200, 100 | 100 | 100 | 25 | 200 | >200 | 100 | 200 | 200 |
| E. coli SK 12140 | 6.3,25 | 25 | 50 | 6 | 12.5, 9 | 6.3 | 3.1 | 3.1 | 3.1 |
| E. coli HH 33779 | 25 | 50 | 50 | 6 | 25 | 25 | 12.5 | 6.3 | 3.1 |
| Kleb. pneumo. SK 4200 | 12.5,25 | 25 | 25 | 6 | 6.3,9 | 12.5 | 1.6 | 1.6 | 1.6 |
| Kleb. pneumo. SK 1200 | 6.3,25 | 50 | 25 | 1.6 | 3.1, 4.7 | 3.1 | 6.3 | 1.6 | 0.4, 0.2 |
| Pseudo. sp. HH 63 | >200 | | | | >200 | >200 | >200 | >200 | >200 |
| Salmonella ATCC 12176 | 12.5 | 13 | 25 | 1.6 | 6.3,9 | 12.5 | 1.6 | 0.8 | 1.6 |
| Shigella HH 117 | 12.5 | 13 | 13 | 1.6 | 6.3,9 | 6.3 | 6.3 | 3.1 | 0.8, 1.6 |
| Entero. aerog. ATCC 13048 | 25,100 | 50 | 100 | 50 | 25 | 50 | 25 | 6.3 | 6.3 |
| Serra. marc. ATCC 13880 | >200 | >200 | >200 | >200 | >200 | >200 | >200 | >200 | >200, 200 |
| Entero. cloacae HH 31254 | 12.5 | — | — | — | 6.3,9 | 12.5 | 3.1 | 3.1 | 3.1, 1.6 |
| Proteus Morgani 179 | >200 | >200 | >200 | >200 | >200 | >200 | >200 | 200 | 200 |

TABLE 2

| Compound | $ED_{50}$ in vivo (mg./kg.) | | | |
|---|---|---|---|---|
| | E. coli 12140 | | Kleb. pneumo. 4200 | |
| | s.c. | p.o. | s.c. | p.o. |
| I | 100 | >200 | — | — |
| II | — | — | — | — |
| III | 9.8,<3 | 78,50 | <3,3 | 50,38 |
| IV | 5.2 | 35 | <3,1.5 | 8.2,10 |
| V | 25 | >200 | >50 | >50 |
| VI | 25 | >200 | 86 | >200 |
| VII | 3 | >50 | 1.1 | 31 |
| VIII | 1.1 | >50 | 0.8,<0.78 | 39 |
| IX | 1 | 41 | 1.5,<3 | 71,50 |

Pharmaceutical compositions having antibacterial activity which comprise a pharmaceutical carrier and a compound of Formula I and methods of producing antibacterial activity by administering a compound of Formula I to an animal in a nontoxic amount sufficient to produce said activity are also objects of this invention. The administration may be orally or by parenteral injection such as subcutaneously, intramuscularly in intravenously. The injection of suitably prepared sterile solutions or suspensions containing an effective, nontoxic amount of the new cephalosporin compound is the preferred route of administration.

The compounds of Formula I are formulated and administered in the same manner as other cephalosporins in dosages of from 250 to 1000 mg. with the total daily dosage being from 1 to 6 g. The precise dosages are dependent upon the age and weight of the subject and on the infection being treated and can be determined by those skilled in the art based on the data disclosed herein compared with that available to the art attained with known cephalosporins.

The following examples illustrate the invention, but are not to be construed as limiting the scope thereof. Temperatures are in degrees of Centigrade unless otherwise stated.

EXAMPLE 1

7-Amino-3-(4-carboxy-1,2,3-triazol-5-ylthiomethyl)-3-cephem-4-carboxylic acid To a solution of 4.6 g. (0.20 mol.) of sodium and 250 ml. of absolute ethanol was added under a nitrogen atmosphere 8.65 g. (0.05 mol.) of 5-amino-4-carbethoxy-1,2,3-thiadiazole. The reaction mixture was stirred one hour, 5 ml. of water was added and the mixture was refluxed for 12 hours. After cooling, the mixture was filtered and the solid product was washed with ethanol and ether and dried to give 4-carboxy-1,2,3-triazole-5-thiol trisodium salt.

4-Carboxy-1,2,3-triazole-5-thiol trisodium salt hydrate (4.4 g., 20 mmol.) was added to a stirred suspension of 4.08 g. (15 mmol.) of 7-aminocephalosporanic acid in 30 ml. of water and 15 ml. of acetone. The reaction mixture was quickly acidified to pH 7.3 with dilute hydrochloric acid, then heated at 65° for 4.5 hours. The mixture was cooled (ice bath), brought to pH 2.4 with dilute hydrochloric acid and the precipitate was collected, washed with water and acetone and dried in vacuo over phosphorus pentoxide to give the title compound.

EXAMPLE 2

7-D-Mandelamido-3-(4-carboxy-1,2,3-triazol-5-ylthiomethyl)-3-cephem-4-carboxylic acid (VI)

A solution of 4.73 g. (16.8 mmol.) of D-O-dichloroacetylmandeloyl chloride in 15 ml. of dry acetone was added dropwise to a cooled ($-15°$) solution of 3.0 g. (8.4 mmol.) of 7-amino-3-(4-carboxy-1,2,3-triazol-5-ylthiomethyl)-3-cephem-4-carboxylic acid in a mixture of 70 ml. of 3% aqueous sodium bicarbonate and 70 ml. of acetone while maintaining the pH between 5.0 and 5.5 by addition of 10% aqueous sodium hydroxide. The reaction mixture was stirred at 25° for 2 hours, then extracted with ether. The aqueous layer was brought to pH 2.0 with 3N hydrochloric acid and the resulting mixture was extracted with ethyl acetate. The ethyl acetate solution was concentrated to about 20 ml. and added dropwise to a rapidly stirred mixture of 200 ml. of ether and 200 ml. of petroleum ether (b.p. 30°-60°). The precipitate was collected and dissolved in ethyl acetate. Chloroform was added, the solution filtered, the filtrate evaporated to dryness, the residue dissolved in 50 ml. of dry methanol and the pH was adjusted to 10.0 by addition of 5% sodium methoxide in methanol at 5°. After 0.5 hour, the pH was adjusted to 7.0 by addition of 2-ethylhexanoic acid, the solution was filtered and the filtrate was diluted with ether to give a precipitate which was collected and dissolved in water. The aqueous solution was filtered and lyophilized to give 7-D-mandelamido-3-(4-carboxy-1,2,3-triazol-5-ylthiomethyl)-3-cephem-4-carboxylic acid disodium salt hydrate.

$C_{19}H_{15}N_5O_7S_2.2$ Na.3.5 $H_2O$: Calculated: 38.13% C; 3.70% H; 11.70% N. Found: 37.95% C; 3.05% H; 11.25% N.

7-D-Mandelamido-3-(4-carboxy-1,2,3-triazol-5-ylthiomethyl)-3-cephem-4-carboxylic acid disodium salt is dissolved in a minimum amount of water to which chloroform is added. While stirring, 3N hydrochloric acid is added until the solution is acidified to pH 2.5. The layers are separated, the aqueous phase is extracted with chloroform and the combined extracts are washed with water, dried ($MgSO_4$) and evaporated to dryness to give the title compound.

EXAMPLE 3

7-(D-α-Aminophenylacetamido)-3-(4-carboxy-1,2,3-triazol-5-ylthiomethyl)-3-cephem-4-carboxylic acid (V)

A solution of 5.05 g. (10 mmol.) of 7-(D-α-t-butoxycarbonylaminophenylacetamido)cephalosporanic acid and 2.84 g. (12.9 mmol.) of 4-carboxy-1,2,3-triazole-5-thiol trisodium salt in 75 ml. of pH 6.4 phosphate buffer solution was heated at 70° for 4.5 hours. The cooled reaction mixture was extracted with ethyl acetate. Fresh ethyl acetate was added and the solution was cooled and acidified to pH 2.0 with 3N hydrochloric acid. The layers were separated and the aqueous phase was reextracted with ethyl acetate. The combined extracts were dried ($MgSO_4$) and evaporated to dryness to give a residue which was chromatographed on silica gel with 8:2:1 chloroform-isopropanol-formic acid as eluant to give 7-(D-α-t-butoxycarbonylaminophenylacetamido)-3-(4-carboxy-1,2,3-triazol-5-ylthiomethyl)-3-cephem-4-carboxylic acid.

7-(D-α-t-butoxycarbonylaminophenylacetamido)-3-(4-carboxy-1,2,3-triazol-5-ylthiomethyl)-3-cephem-4-carboxylic acid was stirred for 45 minutes at 5° in a mixture of 9 ml. of trifluoroacetic acid and 1 ml. of anisole. The mixture was evaporated to dryness and the residue was triturated with ether to give a solid which was dissolved in 125 ml. of water, treated with excess Amberlite IR-45 ion-exchange resin until the pH became constant and lyophilized to give the title compound.

$C_{19}H_{18}N_6O_6S_2.2.25$ $H_2O$: Calculated: 42.97% C; 4.27% H; 15.83% N. Found: 42.99% C; 3.93% H; 15.79% N.

EXAMPLE 4

7-Amino-3-(4-carbethoxy-1,2,3-triazol-5-ylthiomethyl)-3-cephem-4-carboxylic acid To a solution of 100 mg. (0.578 mmol.) of 5-amino-4-carbethoxy-1,2,3-thiadiazole in 4 ml. of absolute ethanol was added 79 mg. (1.16 mmol.) of sodium ethoxide. The mixture was stirred at 25° for 4 hours, then 20 ml. of ether was added and the resulting solid was collected and dried in vacuo over phosphorus pentoxide to give 4-carbethoxy-1,2,3-triazole-5-thiol disodium salt hydrate.

4-Carbethoxy-1,2,3-triazole-5-thiol disodium salt hydrate (3.0 g., 13.8 mmol.) was added to a solution of 2.79 g. (10.2 mmol.) of 7-aminocephalosporanic acid and 1.72 g. (20.5 mmol.) of sodium bicarbonate in 40 ml. of water and 10 ml. of acetone. The reaction mixture was acidified to pH 7.2 with glacial acetic acid then refluxed for 2.5 hours. The cooled mixture was acidified to pH 3.9 with 3N hydrochloric acid and the precipitated solid was collected, washed with water and acetone and dried ($P_2O_5$ in vacuo) to give the title compound.

EXAMPLE 5

7-D-Mandelamido-3-(4-carbethoxy-1,2,3-triazol-5-ylthiomethyl)-3-cephem-4-carboxylic acid When an equivalent amount of 7-amino-3-(4-carbethoxy-1,2,3-triazol-5-ylthiomethyl)-3-cephem-4-carboxylic acid is reacted with D-O-dichloroacetylmandeloyl chloride as described in the procedure of Example 2, the title compound is obtained as the final product.

EXAMPLE 6

7-(D-α-Aminophenylacetamido)-3-(4-carbethoxy-1,2,3-triazol-5-ylthiomethyl)-3-cephem-4-carboxylic acid (II)

Substitution of 4-carbethoxy-1,2,3-triazole-5-thiol disodium salt in the procedure of Example 3 in place of 4-carboxy-1,2,3-traizole-5-thiol trisodium salt gave 7-(D-α-t-butoxycarbonylaminophenylacetamido)-3-(4-carbethoxy-1,2,3-triazol-5-ylthiomethyl)-3-cephem-4-carboxylic acid, which upon treatment with trifluoroacetic acid and anisole as described therein, gave the title compound.

$C_{21}H_{22}N_6O_6S_2.0.5\ C_2HF_3O_2.4H_2O$: Calculated: 40.80% C; 4.75% H; 12.98% N. Found: 40.29% C; 4.02% H; 13.49% N.

EXAMPLE 7

7-(D-α-Amino-4-hydroxyphenylacetamido)-3-(4-carbethoxy-1,2,3-triazol-5-ylthiomethyl)-3-cephem-4-carboxylic acid (I)

When 5.31 g. (10.2 mmol.) of 7-(D-α-t-butoxycarbonylamino-4-hydroxyphenylacetamido)cephalosporanic acid and 3.0 g. (11.5 mmol.) of 4-carbethoxy-1,2,3-triazole-5-thiol disodium salt were substituted in the procedure of Example 3 for 7-(D-α-t-butoxycarbonylaminophenylacetamido)cephalosporanic acid and 4-carboxy-1,2,3-triazole-5-thiol trisodium salt and the resulting 7-(D-α-t-butoxycarbonylamino-4-hydroxyphenylacetamido)-3-(4-carbethoxy-1,2,3-triazol-5-ylthiomethyl)-3-cephem-4-carboxylic acid was treated with trifluoroacetic acid as described therein, the title compound was obtained.

$C_{21}H_{22}N_6O_7S_2.3\ H_2O$ Calculated: 42.85% C; 4.79% H; 14.28% N. Found: 43.30% C; 4.19% H; 13.84% N.

EXAMPLE 8

7-Amino-3-(5-carboxymethyl-1,2,4-triazol-3-ylthiomethyl)-3-cephem-4-carboxylic acid 10% Aqueous sodium hydroxide (8 ml.) was added to a suspension of 5.4 g. (20 mmol.) of 7-aminocephalosporanic acid and 5.5 g. (27 mmol.) of 3-carboxymethyl-1,2,4-triazole-5-thiol disodium salt, prepared by addition of a sodium hydroxide solution to a solution of 3-carboxymethyl-1,2,4-triazole-5-thiol in aqueous ethanol.

The reaction mixture was refluxed for five hours and the ethanol was removed in vacuo. The aqueous residue was cooled and acidified to pH 2.8 with 3N hydrochloric acid. The resulting solid was collected, washed with water and acetone and dried ($P_2O_5$ in vacuo) to give the title compound.

EXAMPLE 9

7-D-Mandelamido-3-(5-carboxymethyl-1,2,4-triazol-3-ylthiomethyl)-3-cephem-4-carboxylic acid (IX)

7-Amino-3-(5-carboxymethyl-1,2,4-triazol-3-ylthiomethyl)-3-cephem-4-carboxylic acid (3.7 g., 10 mmol.) and 5.6 g. (20 mmol.) of D-O-dichloroacetylmandeloyl chloride were reacted as described in the procedure of Example 2. The cooled reaction mixture was extracted with ether, the layers were separated and the pH of the aqueous phase was adjusted to 2.0 by addition of 3N hydrochloric acid. The resulting mixture was extracted with ethyl acetate, the residual solid material was discarded and the organic solution was dried ($MgSO_4$). Addition of ether precipitated a solid which was dissolved in cold 5% aqueous sodium carbonate. The solution was stirred for 20 minutes then acidified to pH 2.0 by addition of 3N hydrochloric acid and extracted with ethyl acetate. The organic phase was dried ($MgSO_4$) and evaporated to dryness to give a residue which was triturated with ethyl acetate to give the title compound.

$C_{20}H_{19}N_5O_7S_2.H_2O$ Calculated: 45.88% C; 4.04% H; 13.38% N. Found: 46.03% C; 3.88% H; 12.94% N.

EXAMPLE 10

7-(D-α-Aminophenylacetamido)-3-(5-carboxymethyl-1,2,4-triazol-3-ylthiomethyl)-3-cephem-4-carboxylic acid (VIII)

Substitution of an equivalent amount of 7-(D-α-t-butoxycarbonylaminophenylacetamido)cephalosporanic acid in the procedure of Example 8 gave 7-(D-α-t-butoxycarbonylaminophenylacetamido)-3-(5-carboxymethyl-1,2,4-triazol-3-ylthiomethyl)-3-cephem-4-carboxylic acid which, upon treatment with trifluoroacetic acid as described in Example 3, gave the title compound.

$C_{20}H_{20}N_6O_6S_2.2\ H_2O$: Calculated: 44.44% C; 4.48% H; 15.55% N. Found: 44.49% C; 4.10% H; 15.28% N.

EXAMPLE 11

7-(D-α-Amino-4-hydroxyphenylacetamido)-3-(5-carboxymethyl-1,2,4-triazol-3-ylthiomethyl)-3-cephem-4-carboxylic acid When 4.38 g. (8.4 mmol.) of 7-(D-α-t-butoxycarbonylamino-4-hydroxyphenylacetamido)cephalosporanic acid and 3-carboxymethyl-1,2,4-triazole-5-thiol were reacted as described in the procedure of Example 8 and the resulting 7-(D-α-t-butoxycarbonylamino-4-hydroxyphenylacetamido)-3-(5-carboxymethyl-1,2,4-triazol-3-ylthiomethyl)-3-cephem-4-carboxylic acid was treated with trifluoroacetic acid as described therein, the title compound was obtained.

$C_{20}H_{20}N_6O_7S_2.4\ H_2O$: Calculated: 40.53% C; 4.76% H; 14.18% N. Found: 39.98% C; 4.11% H; 14.14% N.

EXAMPLE 12

7-Amino-3-(5-carbethoxymethyl-1,2,4-triazol-3-ylthiomethyl)-3-cephem-4-carboxylic acid Reaction of 3-carbethoxymethyl-1,2,4-triazole-5-thiol sodium salt, prepared as described in Example 8, and 7-aminocephalosporanic acid according to the procedure described in Example 8 gives the title compound.

EXAMPLE 13

7-D-Mandelamido-3-(5-carbethoxymethyl-1,2,4-triazol-3-ylthiomethyl)-3-cephem-4-carboxylic acid Substitution of an equivalent amount of 7-amino-3-(5-carbethoxymethyl-1,2,4-triazol-3-ylthiomethyl)-3-cephem-4-carboxylic acid in the procedure of Example 2 for 7-amino-3-(4-carboxy-1,2,3-triazol-5-ylthiomethyl)-3-cephem-4-carboxylic acid gives the title compound.

EXAMPLE 14

7-(D-α-Aminophenylacetamido)-3-(5-carbethoxymethyl-1,2,4-triazol-3-ylthiomethyl)-3-cephem-4-carboxylic acid (III)

The title compound was prepared by use of 3-carbethoxymethyl-1,2,4-triazole-5-thiol sodium salt in place of 3-carboxymethyl-1,2,4-triazol-5-thiol disodium salt in the procedure of Example 8 with subsequent treatment of the 7-(D-α-t-butoxycarbonylaminophenylacetamido)-3-(5-carbethoxymethyl-1,2,4-triazol-3-ylthiomethyl)-3-cephem-4-carboxylic acid with trifluoroacetic acid as described above.

$C_{22}H_{24}N_6O_6S_2.3.5\ H_2O$: Calculated: 44.36% C; 5.25% H; 14.11% N. Found: 44.03% C; 4.47% H; 14.03% N.

EXAMPLE 15

7-(D-α-Amino-4-hydroxyphenylacetamido)-3-(4-carbamoyl-1,2,3-triazol-5-ylthiomethyl)-3-cephem-4-carboxylic acid (IV)

Reaction of 7-(D-α-t-butoxycarbonylamino-4-hydroxyphenylacetamido)cephalosporanic acid, 4-carbamoyl-1,2,3-triazole-5-thiol sodium salt prepared as described in Example 8 and an excess amount of sodium bicarbonate solution according to the procedure described in Example 3 with subsequent treatment of the 7-(D-α-t-butoxycarbonylamino-4-hydroxyphenylacetamido)-3-(4-carbamoyl-1,2,3-triazol-5-ylthiomethyl)-3-cephem-4-carboxylic acid thus formed with trifluoroacetic acid gave the title compound.

$C_{19}H_{19}N_7O_6S_2.2\ H_2O$: Calculated: 42.14% C; 4.28% H; 18.10% N. Found: 42.62% C; 3.97% H; 17.30% N.

EXAMPLE 16

7-Amino-3-(4-carboxymethyl-1,2,4-triazol-3-ylthiomethyl)-3-cephem-4-carboxylic acid To a stirred solution of 2.9 g. (0.02 mol.) of ethyl α-isothiocyanoacetate in 20 ml. of dioxane was added dropwise a solution of 1.20 g. (0.02 mol.) of formylhydrazine in 35 ml. of dioxane. The reaction mixture was stirred for one hour to give 1-carbethoxy-methyl-4-formylthiosemicarbazide.

1-carbethoxy-methyl-4-formylthiosemicarbazide (0.50 g., 2.44 mmol.) was dissolved in 5 ml. of ethanol and 5 ml. (2 equivalents) of aqueous potassium hydroxide solution was added. The reaction mixture was refluxed for five hours then cooled, acidified to pH 2.0 with 6N sulfuric acid and evaporated to dryness. The residue was extracted with acetone to give 4-carboxymethyl-1,2,4-triazole-3-thiol.

Substitution of an equivalent amount of 4-carboxymethyl-1,2,4-triazole-3-thiol in the procedure of Example 8 in place of 3-carboxymethyl-1,2,4-triazol-5-thiol gives the title compound.

EXAMPLE 17

7-D-Mandelamido-3-(4-carboxymethyl-1,2,4-triazol-3-ylthiomethyl)-3-cephem-4-carboxylic acid When 7-amino-3-(4-carboxymethyl-1,2,4-triazol-3-ylthiomethyl)-3-cephem-4-carboxylic acid is used in the procedure of Example 2 in place of 7-amino-3-(4-carboxy-1,2,3-triazol-5-ylthiomethyl)-3-cephem-4-carboxylic acid, the title compound is obtained.

EXAMPLE 18

7-(D-α-Aminophenylacetamido)-3-(4-carboxymethyl-1,2,4-triazol-3-ylthiomethyl)-3-cephem-4-carboxylic acid Reaction of 7-(D-α-t-butoxycarbonylaminophenylacetamido)cephalosporanic acid and 4-carboxymethyl-1,2,4-triazol-3-thiol disodium salt according to the procedure of Example 8 followed by treatment of the 7-(D-α-t-butoxycarbonylaminophenylacetamido)-3-(4-carboxymethyl-1,2,4-triazol-3-ylthiomethyl)-3-cephem-4-carboxylic acid thus obtained with trifluoroacetic acid as described in Example 3, gives the title compound.

EXAMPLE 19

To a solution of 1.725 g. (75 mmol.) of sodium in 50 ml. of absolute ethanol is added 6.0 g. (45 mmol.) of benzylazide and 12.3 g. (50 mmol.) of diethyl 2-(carbomethoxyethyl)malonate. The reaction mixture is refluxed for 12 hours, then cooled and evaporated to dryness. Water (100 ml.) is added and the mixture is heated while maintaining the pH at 12. The aqueous mixture is extracted with ethyl acetate and the aqueous phase is acidified with 3N hydrochloric acid and extracted with ethyl acetate. The ethyl acetate solution is evaporated to dryness to give 1-benzyl-4-(2-carboxyethyl)-5-hydroxy-1,2,3-triazole.

1-Benzyl-4-(2-carboxyethyl)-5-hydroxy-1,2,3-triazole (5.0 g., 0.02 mol.) is suspended in 300 ml. of ethanol. Anhydrous hydrogen chloride gas is bubbled into the suspension for 30 minutes and the mixture is then heated on a steam bath for 20 minutes. The solution is cooled and evaporated to dryness to give a residue which is dissolved in 300 ml. of ethyl acetate. The ethyl acetate solution is washed with water, dried ($MgSO_4$) and evaporated to dryness. Trituration with hexane containing a little acetone gives 1-benzyl-4-(2-carbethoxyethyl)-5-hydroxy-1,2,3-triazole.

To a solution of 1.0 g. (4 mmol.) of 1-benzyl-4-(2-carbethoxyethyl)-5-hydroxy-1,2,3-triazole in 2 ml. of phosphorus oxychloride is added 0.5 g. (5 mmol.) of phosphorus pentachloride. The reaction mixture is stirred at 25° for 2 hours, then warmed on a steam bath for 10 minutes and evaporated to dryness. The residue is dissolved in 0.5 ml. of phosphorus oxychloride and the solution is neated to reflux for 30 minutes, cooled and evaporated to dryness to give 1-benzyl-4-(2-carbethoxyethyl)-5-chloro-1,2,3-triazole.

A solution of 0.54 g. (0.01 mol.) of sodium methoxide in 50 ml. of absolute ethanol is saturated with hydrogen sulfide. 1-Benzyl-4-(2-carbethoxyethyl)-5-chloro-1,2,3-triazole (2.9 g., 0.01 mol.) is added and the reaction mixture is refluxed for 24 hours. The cooled mixture is evaporated to dryness to give 1-benzyl-4-(2-carboxyethyl)-1,2,3-triazole-5-thiol sodium salt. Acidification of an aqueous solution of the triazole thiol salt as previously described gives 1-benzyl-4-(2-carboxyethyl)-1,2,3-triazole-5-thiol.

1-Benzyl-4-carboxyethyl-1,2,3-triazole-5-thiol (1.1 g., 4 mmol.) is suspended in 50 ml. of anhydrous liquid ammonia and sodium is added until a permanent blue color results. The reaction mixture is allowed to stir for 40 minutes then allowed to warm to ambient temperature while the ammonia evaporates. The residue is triturated with ether and the solid formed is collected and dissolved in water. The aqueous solution is acidified and extracted with ethyl acetate. The extract is dried ($MgSO_4$) and evaporated to dryness to give 4-(2-carboxyethyl)-1,2,3-triazol-5-thiol.

4-(2-Carboxyethyl)-1,2,3-triazol-5-thiol is esterified as described hereinabove to give 4-(2-carbethoxyethyl)-1,2,3-triazol-5-thiol.

When an equivalent amount of 4-(2-carboxyethyl)-1,2,3-triazol-5-thiol disodium salt, prepared as in Example 8, is reacted with 7-aminocephalosporanic acid by the procedure of Example 8, 7-amino-3-[4-(2-carboxyethyl)-1,2,3-triazol-5-ylthiomethyl]-3-cephem-4-carboxylic acid is obtained.

In like manner, substitution of 4-(2-carbethoxyethyl)-1,2,3-triazole-5-thiol disodium salt, prepared as previously described, in the procedure of Example 4 for 4-carbethoxy-1,2,3-triazole-5-thiol disodium salt gives 7-amino-3-[4-(2-carbethoxyethyl)-1,2,3-triazol-5-ylthiomethyl]-3-cephem-4-carboxylic acid as the product.

EXAMPLE 20

Substitution of 7-amino-3-[4-(2-carboxyethyl)-1,2,3-triazol-5-ylthiomethyl]-3-cephem-4-carboxylic acid or 7-amino-3-[4-(2-carbethoxyethyl)-1,2,3-triazol-5-ylthiomethyl]-3-cephem-4-carboxylic acid in the procedure of Example 2 for 7-amino-3-(4-carboxy-1,2,3-triazol-5-ylthiomethyl)-3-cephem-4-carboxylic acid gives, respectively, 7-D-mandelamido-3-[4-(2-carboxyethyl)-1,2,3-triazol-5-ylthiomethyl]-3-cephem-4-carboxylic acid and 7-D-mandelamido-3-[4-(2-carbethoxyethyl)-1,2,3-triazol-5-ylthiomethyl]-3-cephem-4-carboxylic acid.

When 7-(D-α-t-butoxycarbonylamino-4-hydroxyphenylacetamido)cephalosporanic acid is reacted with 4-(2-carboxyethyl)-1,2,3-triazole-5-thiol disodium salt or 4-(2-carbethoxyethyl)-1,2,3-triazole-5-thiol sodium salt as described in the procedure of Example 8, and the products formed are de-blocked with trifluoroacetic acid as described above, 7-(D-α-amino-4-hydroxyphenylacetamido)-3-[4-(2-carboxyethyl)-1,2,3-triazol-5-ylthiomethyl]-3-cephem-4-carhoxylic acid and 7-(D-α-amino-4-hydroxyphenylacetamido)-3-[4-(2-carbethoxyethyl)-1,2,3-triazol-5-ylthiomethyl]-3-cephem-4-carboxylic acid are obtained, respectively.

EXAMPLE 21

Use of equivalent amounts of diethyl 2-carbethoxymethylmalonate and diethyl 2-(carbethoxypropyl)malonate, respectively, in the procedure of Example 19 in place of diethyl 2-(carbomethoxyethyl)malonate, followed by the steps of ester hydrolysis, chlorination, sulfide displacement and debenzylation described therein gives 4-carboxymethyl-1,2,3-triazole-5-thiol and 4-(3-carboxypropyl)-1,2,3-triazole-5-thiol.

Esterification of 4-carboxymethyl-1,2,3-triazole-5-thiol and 4-(3-carboxypropyl)-1,2,3-triazole-5-thiol as described in Example 19 gives, respectively, 4-carbethoxymethyl-1,2,3-triazole-5-thiol and 4-(3-carbethoxypropyl)-1,2,3-triazole-5-thiol.

Use of 4-carboxymethyl-1,2,3-triazole-5-thiol disodium salt, 4-(3-carboxypropyl)-1,2,3-triazole-5-thiol disodium salt, 4-carbethoxymethyl-1,2,3-triazole-5-thiol sodium salt or 4-(3-carbethoxypropyl)-1,2,3-triazole-5-thiol sodium salt, all prepared as described in Example 8, in the procedure of Example 8 in place of 3-carboxymethyl-1,2,4-triazole-5-thiol disodium salt, gives the following 7-amino-3-(substituted triazolyl)thiomethyl cephalosporin compounds:

7-amino-3-(4-carboxymethyl-1,2,3-triazol-5-ylthiomethyl)-3-cephem-4-carboxylic acid
7-amino-3-[4-(3-carboxypropyl)-1,2,3-triazol-5-ylthiomethyl]-3-cephem-4-carboxylic acid
7-amino-3-(4-carbethoxymethyl-1,2,3-triazol-5-ylthiomethyl)-3-cephem-4-carboxylic acid
7-amino-3-[4-(3-carbethoxypropyl)-1,2,3-triazol-5-ylthiomethyl]-3-cephem-4-carboxylic acid.

EXAMPLE 22

To a solution of 13.8 g. (0.6 mol.) of sodium in absolute ethanol is added a solution of 96 g. (0.6 mol.) of diethylmalonate in 500 ml. of ether. The mixture is cooled and 117.1 g. (0.6 mol.) of 2-bromo-2-methylpropionic acid ethyl ester is added. The reaction mixture is warmed for two hours, then stirred at ambient temperature for 48 hours. Acetic acid and water are added, the layers are separated and the ethereal phase is washed with water, dried (MgSO$_4$) and evaporated to dryness to give diethyl 2-(1-carbethoxy-1-methylethyl)malonate.

When an equivalent amount of the following bromoesters:

3-bromo-2,2-dimethylpropionic acid methyl ester
5-bromo-2-methylvaleric acid methyl ester
2-bromo-2-ethylbutyric acid methyl ester is used in place of 2-bromo-2-methylpropionic acid ethyl ester in the reaction with diethylmalonate, the substituted malonates listed below are obtained:

diethyl 2-(2-carbomethoxy-2-methylpropyl)malonate
diethyl 2-(4-carbomethoxypentyl)malonate
diethyl 2-(1-carbomethoxy-1-ethylpropyl)malonate.

Substitution of a substituted malonate named hereinabove in place of diethyl 2-(carbomethoxyethyl)malonate as a starting material in the procedure of Example 19 followed by the subsequent synthetic steps described therein, gives the following triazole thiols as products:

4-(1-carboxy-1-methylethyl)-1,2,3-triazole-5-thiol
4-(1-carbethoxy-1-methylethyl)-1,2,3-triazole-5-thiol
4-(2-carboxy-2-methylpropyl)-1,2,3-triazole-5-thiol
4-(2-carbethoxy-2-methylpropyl)-1,2,3-triazole-5-thiol
4-(4-carboxypentyl)-1,2,3-triazole-5-thiol
4-(4-carbethoxypentyl)-1,2,3-triazole-5-thiol
4-(1-carboxy-1-ethylpropyl)-1,2,3-triazole-5-thiol
4-(1-carbethoxy-1-ethylpropyl)-1,2,3-triazole-5-thiol.

Use of an ester substituted triazole thiol sodium salt or an acid substituted triazole thiol disodium salt, prepared as described above, in the procedure of Example 8 in place of 3-carboxymethyl-1,2,4-triazole-5-thiol disodium salt gives the following 7-amino-3-(substituted triazolyl)thiomethyl cephalosporin compounds:

7-amino-3-[4-(1-carboxy-1-methylethyl)-1,2,3-triazol-5-ylthiomethyl]-3-cephem-4-carboxylic acid
7-amino-3-[4-(1-carbethoxy-1-methylethyl)-1,2,3-triazol-5-ylthiomethyl]-3-cephem-4-carboxylic acid
7-amino-3-[4-(2-carboxy-2-methylpropyl)-1,2,3-triazol-5-ylthiomethyl]-3-cephem-4-carboxylic acid
7-amino-3-[4-(2-carbethoxy-2-methylpropyl)-1,2,3-triazol-5-ylthiomethyl]-3-cephem-4-carboxylic acid
7-amino-3-[4-(4-carboxypentyl)-1,2,3-triazol-5-ylthiomethyl]-3-cephem-4-carboxylic acid
7-amino-3-[4-(4-carbethoxypentyl)-1,2,3-triazol-5-ylthiomethyl]-3-cephem-4-carboxylic acid
7-amino-3-[4-(1-carboxy-1-ethylpropyl)-1,2,3-triazol-5-ylthiomethyl]-3-cephem-4-carboxylic acid
7-amino-3-[4-(1-carbethoxy-1-ethylpropyl)-1,2,3-triazol-5-ylthiomethyl]-3-cephem-4-carboxylic acid.

EXAMPLE 23

Substitution of a 7-amino-3-(substituted triazolyl)thiomethyl cephalosporin listed in Examples 21 and 22 in the procedure of Example 2 for 7-amino-3-(4-carboxy- 1,2,3-triazol-5-ylthiomethyl)-3-cephem-4-carboxylic acid gives the following 7-mandelamidocephalosporins:

7-D-mandelamido-3-(4-carboxymethyl-1,2,3-triazol-5-ylthiomethyl)3-cephem-4-carboxylic acid
7-D-mandelamido-3-[4-(3-carboxypropyl)-1,2,3-triazol-5-ylthiomethyl]-3-cephem-4-carboxylic acid
7-D-mandelamido-3-(4-carbethoxymethyl-1,2,3-triazol-5-ylthiomethyl)-3-cephem-4-carboxylic acid
7-D-mandelamido-3-[4-(3-carbethoxypropyl)-1,2,3-triazol-5-ylthiomethyl]-3-cephem-4-carboxylic acid
7-D-mandelamido-3-[4-(1-carboxy-1-methylethyl)-1,2,3-triazol-5-ylthiomethyl]-3-cephem-4-carboxylic acid
7-D-mandelamido-3-[4-(1-carbethoxy-1-methylethyl)-1,2,3-triazol-5-ylthiomethyl]-3-cephem-4-carboxylic acid
7-D-mandelamido-3-[4-(2-carboxy-2-methylpropyl)-1,2,3-triazol-5-ylthiomethyl]-3-cephem-4-carboxylic acid
7-D-mandelamido -3-[4-(2-carbethoxy-2-methylpropyl)-1,2,3-triazol-5-ylthiomethyl]-3-cephem-4-carboxylic acid
7-D-mandelamido-3-[4-(4-carboxypentyl)-1,2,3-triazol-5-ylthiomethyl]-3-cephem-4-carboxylic acid
7-D-mandelamido-3-[4-(4-carbethoxypentyl)-1,2,3-triazol-5-ylthiomethyl]-3-cephem-4-carboxylic acid
7-D-mandelamido-3-[4-(1-carboxy-1-ethylpropyl)-1,2,3-triazol-5-ylthiomethyl]-3-cephem-4-carboxylic acid
7-D-mandelamido-3-[4-(1-carbethoxy-1-ethylpropyl)-1,2,3-triazol-5-ylthiomethyl]-3-cephem-4-carboxylic acid.

Likewise, reaction of a substituted triazole thiol mono- or disodium salt from Examples 21 and 22 with 7-(D-α-t-butoxycarbonylaminophenylacetamido)cephalosporanic acid or 7-(D-α-t-butoxycarbonylamino-4-hydroxyphenylacetamido)cephalosporanic acid according to the procedure of Example 8 with subsequent removal of the protective group as described above, gives the corresponding 7-(D-α-aminophenylacetamido)-3-(carboxy and carbethoxytriazolylthiomethyl)-3-cephem-4-carboxylic acids and 7-(D-α-amino-4-hydopxyphenylacetamido)-3-(carboxy and carbethoxytriazolylthiomethyl)-3-cephem-4-carboxylic acids.

EXAMPLE 24

4-Carbomethoxymethyl-1,2,3-triazole, 4-carboisopropoxymethyl-1,2,3-triazole-5-thiol and 4-carbo-t-butoxymethyl-1,2,3-triazole-5-thiol are prepared by esterification of 4-carboxymethyl-1,2,3-triazole-5-thiol according to any of the esterification methods well known to the art.

Preparation and use of 4-carbomethoxymethyl-1,2,3-triazole-5-thiol sodium salt in the procedure of Example 8 gives 7-amino-3-(4-carbomethoxymethyl-1,2,3-triazol-5-ylthiomethyl)-3-cephem-4-carboxylic acid.

Similarly, preparation and use of 4-carboisopropoxymethyl-1,2,3-triazole-5-thiol sodium salt in the procedure of Example 8 gives 7-amino-3-(4-carboisopropoxymethyl-1,2,3-triazol-5-ylthiomethyl)-3-cephem-4-carboxylic acid.

In like manner, when 4-carbo-t-butoxymethyl-1,2,3-triazole-5-thiol disodium salt is prepared and used in Example 8, 7-amino-3-(4-carbo-t-butoxymethyl-1,2,3-triazol-5-ylthiomethyl)-3-cephem-4-carboxylic acid is obtained.

EXAMPLE 25

When 7-amino-3-(4-carbomethoxymethyl-1,2,3-triazol-5-ylthiomethyl)-3-cephem-4-carboxylic acid, 7-amino-3-(4-carboisopropoxymethyl-1,2,3-triazol-5-ylthiomethyl)-3-cephem-4-carboxylic acid or 7-amino-3-(4-carbo-t-butoxymethyl-1,2,3-triazol-5-ylthiomethyl)-3-cephem-4-carboxylic acid is used in the procedure of Example 2 in place of 7-amino-3-(4-carboxy-1,2,3-triazol-5-ylthiomethyl)-3-cephem-4-carboxylic acid, 7-D-mandelamido-3-(4-carbomethoxy-1,2,3-triazol-5-ylthiomethyl)-3-cephem-4-carboxylic acid, 7-D-mandelamido-3-(4-carboisopropoxymethyl-1,2,3-triazol-5-ylthiomethyl)-3-cephem-4-carboxylic acid and 7-D-mandelamido-3-(4-carbo-t-butoxymethyl-1,2,3-triazol-5-ylthiomethyl)-3-cephem-4-carboxylic acid are obtained, respectively.

EXAMPLE 26

Reaction of 4-carbomethoxymethyl-1,2,3-triazole-5-thiol sodium salt, 4-carboisopropoxymethyl-1,2,3-triazole-5-thiol sodium salt or 4-carbo-t-butoxymethyl-1,2,3-triazole-5-thiol sodium salt with 7-(D-α-t-butoxycarbonylaminophenylacetamido)cephalosporanic acid as described in the procedure of Example 8 with subsequent removal of the protective group as described in Example 3 gives, respectively, 7-(D-α-aminophenylacetamido)-3-(4-carbomethoxymethyl-1,2,3-triazol-5-ylthiomethyl)-3-cephem-4-carboxylic acid, 7-(D-α-aminophenylacetamido)-3-cephem-4-carboxylic acid and 7-(D-α-aminophenylacetamido)-3-(4-carbo-t-butoxymethyl-1,2,3-triazol-5-ylthiomethyl)-3-cephem-4-carboxylic acid.

EXAMPLE 27

Substitution of 7-(D-α-t-butoxycarbonylamino-4-hydroxyphenylacetamido)cephalosporanic acid and 4-carbomethoxymethyl-1,2,3-triazole-5-thiol sodium salt, 4-carboisopropoxymethyl-1,2,3-triazol-5-triol sodium salt or 4-carbo-t-butoxymethyl-1,2,3-triazole-5-thiol sodium salt in the procedure of Example 8 followed by removal of the protective group as described above gives 7-(D-α-amino-4-hydroxyphenylacetamido)-3-(4-carbomethoxymethyl-1,2,3-triazol-5-ylthiomethyl)-3-cephem-4-carboxylic acid, 7-(D-α-amino-4-hydroxyphenylacetamido)-3-(4-carboisopropoxymethyl-1,2,3-triazol-5-ylthiomethyl)-3-cephem-4-carboxylic acid and 7-(D-α-amino-4-hydroxyphenylacetamido)-3-(4-carbo-t-butoxymethyl-1,2,3-triazol-5-ylthiomethyl)-3-cephem-4-carboxylic acid, respectively.

EXAMPLE 28

7-amino-3-(4-carbamoyl-1,2,3-triazol-5-ylthiomethyl)-3-cephem-4-carboxylic acid

Reaction of 4-carbamoyl-1,2,3-triazole-5-thiol sodium salt and 7-aminocephalosporanic acid as described hereinabove gives the title compound.

EXAMPLE 29

Reaction of the t-butoxycarbonyl derivative of the following cephalosporanic acids:

7-(α-amino-4-chlorophenylacetamido)cephalosporanic acid 7-(α-amino-4-nitrophenylacetamido)cephalosporanic acid
7-(α-amino-3-trifluoromethylphenylacetamido)cephalosporanic acid
7-(α-amino-4-methylphenylacetamido)cephalosporanic acid  7-(α-amino-4-isopropylphenylacetamido)cephalosporanic acid
7-(α-amino-4-bromophenylacetamido)cephalosporanic acid
7-(α-amino-3-fluorophenylacetamido)cephalosporanic acid
7-(α-amino-2-chlorophenylacetamido)cephalosporanic acid
7-(α-amino-4-hydroxymethylphenylacetamido)cephalosporanic acid
7-(α-amino-4-formamidophenylacetamido)cephalosporanic acid
7-(α-amino-3-formamidophenylacetamido)cephalosporanic acid with a 3-carboxymethyl-1,2,4-triazole-5-thiol disodium salt as described in the procedure of Example 8 followed by removal of the protective group as described therein gives the following compounds:

7-(α-amino-4-chlorophenylacetamido)-3-(5-carboxymethyl-1,2,4-triazol-3-ylthiomethyl)-3-cephem-4-carboxylic acid
7-(α-amino-4-nitrophenylacetamido)-3-(5-carboxymethyl-1,2,4-triazol-3-ylthiomethyl)-3-cephem-4-carboxylic acid
7-(α-amino-3-trifluoromethylphenylacetamido)-3-(5-carboxymethyl-1,2,4-triazol-3-ylthiomethyl)-3-cephem-4-carboxylic acid
7-(α-amino-4-methylphenylacetamido)-3-(5-carboxymethyl-1,2,4-triazol-3-ylthiomethyl)-3-cephem-4-carboxylic acid
7-(α-amino-4-isopropylphenylacetamido)-3-(5-carboxymethyl-1,2,4-triazol-3-ylthiomethyl)-3-cephem-4-carboxylic acid
7-(α-amino-4-bromophenylacetamido)-3-(5-carboxymethyl-1,2,4-triazol-3-ylthiomethyl)-3-cephem-4-carboxylic acid
7-(α-amino-3-fluorophenylacetamido)-3-(5-carboxymethyl-1,2,4-triazol-3-ylthiomethyl)-3-cephem-4-carboxylic acid
7-(α-amino-2-chlorophenylacetamido)-3-(5-carboxymethyl-1,2,4triazol-3-ylthiomethyl)-3-cephem-4-carboxylic acid
7-(α-amino-4-hydroxymethylphenylacetamido)-3-(5-carboxymethyl-1,2,4-triazol-3-ylthiomethyl)-3-cephem-4-carboxylic acid
7-(α-amino-4-formamdiophenylacetamido)-3-(5-carboxymethyl-1,2,4-triazol-3-ylthiomethyl)-3-cephem-4-carboxylic acid
7-(α-amino-3-formamidophenylacetamido)-3-(5-carboxymethyl-1,2,4-triazol-3-ylthiomethyl)-3-cephem-4-carboxylic acid.

By similar procedures described hereinabove, 7-(α-amino-monosubstituted phenylacetamido)-3-(5-carbethoxymethyl-1,2,4-triazol-3-ylthiomethyl)-3-cephem-4-carboxylic acids, 7-(α-amino-monosubstituted phenylacetamido)-3-(4-carbamoyl-1,2,3-triazol-5-ylthiomethyl)-3-cephem-4-carboxylic acids and 7-(α-amino-monosubstituted phenylacetamido)-3-(4-carboxy-1,2,3-triazol-5-ylthiomethyl)-3-cephem-4-carboxylic acids are prepared by reaction of the t-butoxycarbonyl derivative of the cephalosporanic acids listed above with 3-carbethoxymethyl-1,2,4-triazole-5-thiol sodium salt, 4-carbemoyl-1,2,3-triazoie-5-thiol sodium salt or 4-carboxy-1,2,3-triazole-5-triol trisodium salt, respectively, followed by removal of the protective groups as peviously described.

EXAMPLE 30

Reaction of the t-butoxycarbonyl derivative of the following cephalosporanic acids:

7-(α-amino-3,4-dichlorophenylacetamido)cephalosporanic acid
7-(α-amino-3,4-dimethoxyphenylacetamido)cephalosporanic acid
7-(α-amino-3,5-dihydroxyphenylacetamido)cephalosporanic acid
7-(α-amino-3-chloro-4-hydroxyphenylacetamido)cephalosporanic acid
7-(α-amino-2-chloro-4-hydroxyphenylacetamido)cephalosporanic acid
7-(α-amino-2-fluoro-4-hydroxyphenylacetamido)cephalosporanic acid
7-(α-amino-3-fluoro-4-hydroxyphenylacetamido)cephalosporanic acid
7-(α-amino-4hydroxy-3-methoxyphenylacetamido)-cephalosporanic acid
7-(α-amino-3-hydroxy-4-methoxyphenylacetamido)-cephalosporanic acid with 4-carbamoyl-1,2,3-triazole-5-thiol sodium salt as described in the procedure of Example 8 followed by removal of the protective group as described hereinabove gives the following compounds:

7-(α-amino-3,4-dichlorophenylacetamido)-3-(4-carbamoyl-1,2,3-triazol-5-ylthiomethyl)-3-cephem-4-carboxylic acid
7-(α-amino-3,4-dimethoxyphenylacetamido)-3-(4-carbamoyl-1,2,3-triazol-5-ylthiomethyl)-3-cephem-4-carboxylic acid
7-(α-amino-3,5-dihydroxyphenylacetamido)-3-(4-carbamoyl-1,2,3-triazol-5-ylthiomethyl)-3-cephem-4-carboxylic acid
7-(α-amtno-3-chloro-4-hydroxyphenylacetamido)-3-(4-carbamoyl-1,2,3-triazol-5-ylthiomethyl)-3-cephem-4-carboxylic acid
7-(α-amino-2-chloro-4-hydroxyphenylacetamido)-3-(4-carbamoyl-1,2,3-triazol-5-ylthiomethyl)-3-cephem-4-carboxylic acid
7-(α-amino-2-fluoro-4-hydroxyphenylacetamido)-3-4-carbamoyl-1,2,3-triazol-5-ylthiomethyl)-3-cephem-4-carboxylic acid
7-(α-amino-3-fluoro-4-hydroxyphenylacetamido)-3-(4-carbamoyl-1,2,3-triazol-5-ylthiomethyl)-3-cephem-4-carboxylic acid
7-(α-amino-4-hydroxy-3-methoxyphenylacetamido)-3-(4-carbamoyl-1,2,3-triazol-5-ylthiomethyl)-3-cephem-4-carboxylic acid
7-(α-amino-3-hydroxy-4-methoxyphenylacetamido)-3-(4-carbamoyl-1,2,3-triazol-5-ylthiomethyl)-3-cephem-4-carboxylic acid.

Likewise, reaction of the t-butoxycarbonyl derivative of the cephalosporanic acids listed above with 3-carbethoxymethyl-1,2,4-triazole-5-thiol sodium salt, 3-carboxymethyl-1,2,4-triazole-5-thiol disodium salt or 4-carboxy-1,2,3-triazol-5-thiol trisodium salt by procedures described hereinabove with subsequent deblocking of the products thus formed as previously described, gives the corresponding 7-(α-amino-disubstituted phenylacetamido)-3-(5-carbethoxymethyl-1,2,4-triazol-3-ylthiomethyl-, 5-carboxymethyl-1,2,4-triazol-3-ylthiomethyl- and 4-carboxy-1,2,3-triazol-5-ylthiomethyl)-3-cephem-4-carboxylic acids of this invention, respectively.

EXAMPLE 31

Reaction of a substituted mandelamido cephalosporanic acid listed below:

7-(3,4-dichloromandelamido)cephalosporanic acid
7-(4-methylmandelamido)cephalosporanic acid
7-(3,4-dimethoxymandelamido)cephalosporanic acid
7-(4-isopropylmandelamido)cephalosporanic acid
7-(4-bromomandelamido)cephalosporanic acid
7-(3-fluoromandelamido)cephalosporanic acid
7-(4-nitromandelamido)cephalosporanic acid
7-(2-chloromandelamido)cephalosporanic acid
7-(4-aminomandelamido)cephalosporanic acid
7-(3-trifluoromethylmandelamido)cephalosporanic acid
7-(4-hydroxymandelamido)cephalosporanic acid with a 3-carboxymethyl-1,2,4-triazole-5-thiol disodium salt as described in the procedure of Example 8 gives the following compounds of this invention as final products, respectively:

7-(3,4-dichloromandelamido)-3-(5-carboxymethyl-1,2,4-triazol-3-ylthiomethyl)-3-cephem-4-carboxylic acid
7-(4-methylmandelamido)-3-(5-carboxymethyl-1,2,4-triazol-3-ylthiomethyl)-3-cephem4-carboxylic acid
7-(3,4-dimethoxymandelamido)-3-(5-carboxymethyl-1,2,4-triazol-3-ylthiomethyl)-3-cephem-4-carboxylic acid
7-(4-isopropylmandelamido)-3-(5-carboxymethyl-1,2,4-triazol-3-ylthiomethyl)-3-cephem-4-carboxylic acid
7-(4-bromomandelamido)-3-(5-carboxymethyl-1,2,4-triazol-3-ylthiomethyl)-3-cephem-4-carboxylic acid
7-(3-fluoromandelamido)-3-(5-carboxymethyl-1,2,4-triazol-3-ylthiomethyl)-3-cephem-4-carboxylic acid
7-(4-nitromandelamido)-3-(5-carboxymethyl-1,2,4-triazol-3-ylthiomethyl)-3-cephem-4-carboxylic acid
7-(2-chloromandelamido)-3-(5-carboxymethyl-1,2,4-triazol-3-ylthiomethyl)-3-cephem-4-carboxylic acid
7-(4-aminomandelamido)-3-(5-carboxymethyl-1,2,4-triazol-3-ylthiomethyl)-3-cephem-4-carboxylic acid
7-(3-trifluoromethylmandelamido)-3-(5-carboxymethyl-1,2,4-triazol-3-ylthiomethyl)-3-cephem-4-carboxylic acid
7-(4-hydroxymandelamido)-3-(5-carboxymethyl-1,2,4-triazol-3-ylthiomethyl)-3-cephem-4-carboxylic acid.

Similarly, 7-(substituted mandelamido)-3-(5-carbethoxymethyl-1,2,4-triazol-3-ylthiomethyl-, 4-carbamoyl-1,2,3-triazol-5-ylthiomethyl- and 4-carboxy-1,2,3-triazol-5-ylthiomethyl)-3-cephem-4-carboxylic acids are prepared by reaction of a substituted mandelamido cephalosporanic acid listed above with 3-carbethoxymethyl-1,2,4-triazole-5-thiol sodium salt, 4-carbamoyl-1,2,3-triazole-5-thiol sodium salt or 4-carboxy-1,2,3-triazole-5-thiol trisodium salt, respectively, according to procedure described hereinabove.

EXAMPLE 32

Reaction of 7-(α-hydroxythienylacetamido)-cephalosporanic acid and the mono-, di- or trisodium salt of a triazole thiol listed below:

3-carbethoxymethyl-1,2,4-triazole-5-thiol
3-carboxymethyl-1,2,4-triazole-5-thiol
4-carbamoyl-1,2,3-triazole-5-thiol
4-carboxy-1,2,3-triazole-5-thiol as described in the prodecures of Examples 3 or 8 gives the following compounds of this invention, respectively:

7-(α-hydroxythienylacetamido)-3-(5-carbethoxymethyl-1,2,4-triazol-3-ylthiomethyl)-3-cephem-4-carboxylic acid
7-(α-hydroxythienylacetamido)-3-(5-carboxymethyl-1,2,4-triazol-3-ylthiomethyl)-3-cephem-4-carboxylic acid
7-(α-hydroxythienylacetamido)-3-(4-carbamoyl-1,2,3-triazol-5-ylthiomethyl)-3-cephem-4-carboxylic acid
7-(α-hydroxythienylacetamido)-3-(4-carboxy-1,2,3-triazol-5-ylthiomethyl)-3-cephem-4-carboxylic acid.

EXAMPLE 33

When the t-butoxycarbonyl derivative of 7-(α-aminothienylacetamido)cephalosporanic acid is reacted with the mono-, di- or trisodium salt of a triazole thiol listed in Example 32 according to the procedures of Examples 3 or 8 and the resulting product is de-blocked as described above, the following cephalosporin products are obtained, respectively:

7-(α-aminothienylacetamido)-3-(5-carbethoxymethyl-1,2,4-triazol-3-ylthiomethyl)-3-cephem-4-carboxylic acid
7-(α-aminothienylacetamido)-3-(5-carboxymethyl-1,2,4-triazol-3-ylthiomethyl)-3-cephem-4-carboxylic acid
7-(α-aminothienylacetamido)-3-(4-carbamoyl-1,2,3-triazol-5-ylthiomethyl)-3-cephem-4-carboxylic acid
7-(α-aminothienylacetamido)-3-(4-carboxy-1,2,3-triazol-5-ylthiomethyl)-3-cephem-4-carboxylic acid.

EXAMPLE 34

A mixture of 2.5 g. (7.7 mmol.) of D-α-(N-t-butoxycarbonyl)-4-aminophenylglycine, 1.8 g. (9.2 mmol.) of α-bromoacetic acid t-butyl ester and 2.5 g. (19.3 mmol.) of diisopropyl ethylamine in 15 ml. of ethanol was stirred at 25° for 48 hours. The solvent was removed in vacuo, the residue was diluted with ethyl acetate and sodium bicarbonate and the pH was adjusted to 2.5. The layers were separated and the aqueous phase was again extracted with ethyl acetate. The combined extracts were washed with saturated sodium chloride solution, dried (MgSO$_4$) and evaporated to dryness to give D-c-(N-t-butoxycarbonyl)-4-t-butoxycarbonylmethylaminophenylglycine.

A solution of 0.380 g. (1.0 mmol.) of D-α-(N-t-butoxycarbonyl)-4t-butoxycarbonylmethylaminophenylglycine, 0.296 g. (1.0 mmol.) of 7-aminocephalosporanic acid t-butyl ester and b 0.210 g. (1.0 mmol.) of dicyclohexylcarbodiimide in 25 ml. of 9:1 ethyl acetate-methylene chloride is stirred at 0° for 1 hour. The reaction mixture is filtered and the filtrate is washed with 2.5% sulfuric acid, 5% sodium bicarbonate and water, dried (MgSO$_4$) and concentrated to give 7-(D-60 -t-butoxycarbonylamino-4-carboxymethylaminophenylacetamido)cephalosporanic acid t-butyl ester. De-blocking is accomplished by stirring a mixture of the cephalosporanic acid t-butyl ester and 2 ml. of benzenethiol in 10 ml. of trifluoroacetic acid at 25° for 1 hour. Evaporation of the reaction mixture to dryness gives 7-(D-α-amino-4-carboxymethylaminophenylacetamido)cephalosporanic acid.

Reaction of the t-butoxycarbonyl derivative of 7-(D-α-amino-4-carboxymethylaminophenylacetamido)cephalosporanic acid with the mono-, di- or trisodium salt of a triazole thiol listed in Example 32 according to the procedures of Examples 3 or 8 with subsequent removal of the protective group as described herein gives the following substituted cephalosporin compounds of this invention:

7-(D-α-amino-4-carboxymethylaminophenylacetamido)-3-(5-carbethoxymethyl-1,2,4-triazol-3-ylthiomethyl)-3-cephem-4-carboxylic acid
7-(D-α-amino-4-carboxymethylaminophenylacetamido)-3-(5-carboxymethyl-1,2,4-triazol-3-ylthiomethyl)-3-cephem-4-carboxylic acid
7-(D-α-amino-4-carboxymethylaminophenylacetamido)-3-(4-carbamoyl-1,2,3-triazol-5-ylthiomethyl)-3-cephem-4-carboxylic acid
7-(D-α-amino-4-carboxymethylaminophenylacetamido)-3-(4-carboxy-1,2,3-triazol-5-ylthiomethyl)-3-cephem-4-carboxylic acid.

EXAMPLE 35

A solution of 7.2 g. (44 mmol.) of 1,1-carbonyldiimidazole in 110 ml. of dry tetrahydrofuran and 20 ml. of dimethylformamide is added to a solution of 7.7 g. (43.8 mmol.) of 4-carboxy-1,2,3-triazol-5-thiol in 110 ml. of dry tetrahydrofuran and 20 ml. of dimethylformamide. Tetrahydrofuran saturated with methylamine is added and the reaction mixture is stirred at 25° for 12 hours. The mixture is evaporated to dryness, the residue is diluted with 200 ml. of water and the resulting solution is adjusted to pH 2–3 by addition of sulfuric acid. The aqueous solution is lyophilized and the residue extracted with acetone to give 4-N-methylcarbamoyl-1,2,3-triazole-5-thiol.

Reaction of 4-N-methylcarbamoyl-1,2,3-triazole-5-thiol sodium salt, prepared as described in Example 8, with 7-aminocephalosporanic acid, 7-D-mandelamidocephalosporanic acid, 7-(D-α-t-butoxycarbonylaminophenylacetamido)cephalosporanic acid and 7-(D-α-t-butoxycarbonylamino-4-hydroxphenylacetamido)cephalosporanic acid, respectively, with removal of the protective groups when necessary as described hereinabove, gives the following compounds of this invention:

7-amino-3-(4-N-methylcarbamoyl-1,2,3-triazol-5-ylthiomethyl)-3-cephem-4-carboxylic acid
7-D-mandelamido-3-(4-N-methylcarbamoyl-1,2,3-triazol-5-ylthiomethyl)-3-cephem-4-carboxylic acid
7-(D-α-aminophenylacetamido)-3-(4-N-methylcarbamoyl-1,2,3-triazol-5-ylthiomethyl)-3-cephem-4-carboxylic acid
7-(D-α-amino-4-hydroxyphenylacetamido)-3-(4-N-methylcarbamoyl-1,2,3-triazol-5-ylthiomethyl)-3-cephem-4-carboxylic acid.

Example 36

To a solution of 5.34 g. (33.8 mmol.) of 3-carboxymethyl-1,2,4-triazole-5-thiol in 75 ml. of dry tetrahydrofuran and 20 ml. of dry dimethylformamide is slowly added a solution of 5.49 g. (33.9 mmol.) of 1,1-carbonyldiimidazole in 95 ml. of dry dimethylformamide. The reaction mixture is stirred for 35 minutes, then 250 ml. of tetrahydrofuran saturated with dimethylamine is added to the suspension and it is stirred 25° for 12 hours. The mixture is concentrated to about 200 ml. and tetrahydrofuran and ether are added. The precipitate is collected by filtration and dissolved in 170 ml. of water. The aqueous solution is acidified to pH 2.0 by addition of 6N sulfuric acid and extracted with ethyl acetate. The ethyl acetate solution is evaporated to dryness to give 3-N,N-dimethylcarbamoylmethyl-1,2,4-triazole-5-thiol.

Reaction of 3-N,N-dimethylcarbamoylmethyl-1,2,4-traizole-5-thiol sodium salt, prepared as described in Example 8, with 7-aminocephalosporanic acid, 7-D-mandelamidocephalosporanic acid, 7-(D-α-t-butoxycarbonylaminophenylacetamido)cephalosporanic acid and 7-(D-α-t-butoxycarbonylamino-4-hydroxyphenylacetamido)cephalosporanic acid, respectively, with removal of the protective groups when necessary as described hereinabove, gives the following compounds of this invention;

7-amino-3-(5-N,N-dimethylcarbamoylmethyl-1,2,4-triazol-3-ylthiomethyl)-3-cephem-4-carboxylic acid
7-D-mandelamido-3-(5-N,N-dimethylcarbamoylmethyl-1,2,4-triazol-3-ylthiomethyl)-3-cephem-4-carboxylic acid
7-(D-α-aminophenylacetamido)-3-(5-N,N-dimethylcarbamoylmethyl-1,2,4-triazol-3-ylthiomethyl)-3-cephem-4-carboxylic acid
7-(D-α-amino-4-hydroxyphenylacetamido)-3-(5-N,N-dimethylcarbamoylmethyl-1,2,4-triazole-3-ylthiomethyl)-3-cephem-4-carboxylic acid.

EXAMPLE 37

When ethylamine, propylamine or butylamine is substituted for methylamine in the procedure for Example 35, the following triazole thiols are prepared:

4-N-ethylcarbamoyl-1,2,3-triazole-5-thiol
4-N-propylcarbamoyl-1,2,3-triazole-5-thiol
4-N-butylcarbamoyl-1,2,3-triazole-5-thiol.

Reaction of the sodium salt of a triazole thiol listed above, prepared as described in Example 8, with 7-aminocephalosporamic acid, 7-D-mandelamidocephalosporanic acid, 7-(D-α-t-butoxycarbonylaminophenylacetamido)cephalosporanic acid and 7-(D-α-t-butoxycarbonylamino-4-hydroxyphenylacetamido)-cephalosporanic acid, respectively, with removal of the protective groups when necessary as described hereinabove, gives the following compounds of this invention:

7-amino-3-(4-N-ethylcarbamoyl-1,2,3-triazol-5-ylthiomethyl)-3-cephem-4-carboxylic acid
7-amino-3-(4-N-propylcarbamoyl-1,2,3-triazol-5-ylthiomethyl)-3-cephem-4-carboxylic acid
7-amino-3-(4-N-butylcarbamoyl-1,2,3-triazol-5-ylthiomethyl)-3-cephem-4-carboxylic acid
7-D-mandelamido-3-(4-N-ethylcarbamoyl-1,2,3-triazol-5-ylthiomethyl)-3-cephem-4-carboxylic acid 7-D-mandelamido-3-(4-N-propylcarbamoyl-1,2,3-triazol-5-ylthiomethyl)-3-cephem-4-carboxylic acid
7-D-mandelamido-3-(4-N-butylcarbamoyl-1,2,3-triazol-5-ylthiomethyl)-3-cephem-4-carboxylic acid
7-(D-α-aminophenylacetamido)-3-(4-N-ethylcarbamoyl-1,2,3-triazol-5-ylthiomethyl)-3-cephem-4-carboxylic acid
7-(D-α-aminophenylacetamido)-3-(4-N-propylcarbamoyl-1,2,3-triazol-5-ylthiomethyl)-3-cephem-4-carboxylic acid
7-(D-α-aminophenylacetamido)-3-(4-N-butylcarbamoyl-1,2,3-triazol-5-ylthiomethyl)-3-cephem-4-carboxylic acid
7-(D-α-amino-4-hydroxyphenylacetamido)-3-(4-N-ethylcarbamoyl-1,2,3-triazol-5-ylthiomethyl)-3-cephem-4-carboxylic acid
7-(D-α-amino-4-hydroxyphenylacetamido)-3-(4-N-propylcarbamoyl-1,2,3-triazol-5-ylthiomethyl)-3-cephem-4-carboxylic acid
7-(D-α-amino-4-hydroxyphenylacetamido)-3-(4-N-butylcarbamoyl-1,2,3-triazol-5-ylthiomethyl)-3-cephem-4-carboxylic acid.

EXAMPLE 38

When diethylamine, dipropylamine or dibutylamine is substituted for dimethylamine in the procedure of Example 36, the following triazole thiols are prepared:

3-N,N-diethylcarbamoylmethyl-1,2,4-triazole-5-thiol
3-N,N-dipropylcarbamoylmethyl-1,2,4-triazole-5-thiol
3-N,N-dibutylcarbamoylmethyl-1,2,4-triazole-5-thiol.

Reaction of the sodium salt of a triazole thiol listed above, prepared as described in Example 8, with 7-aminocephalosporanic acid, 7-D-mandelamidocephalosporanic acid, 7-(D-α-t-butoxycarbonylaminophenylacetamido)cephalosporanic acid and 7-(D-α-t-butoxycarbonylamino-4-hydroxyphenylacetamido)-cephalosporanic acid, respectively, with removal of the protective groups when necessary as described hereinabove, gives the following compounds of this invention:

7-amino-3-(5-N,N-diethylcarbamoylmethyl-1,2,4-triazol-3-ylthiomethyl)-3-cephem-4-carboxylic acid
7-amino-3-(5-N,N-dipropylcarbamoylmethyl-1,2,4-triazol-3-ylthiomethyl)-3-cephem-4-carboxylic acid
7-amino-3-(5-N,N-dibutylcarbamoylmethyl-1,2,4-triazol-3-ylthiomethyl)-3-cephem-4-carboxylic acid
7-D-mandelamido-3-(5-N,N-diethylcarbamoylmethyl-1,2,4-triazol-3-ylthiomethyl)-3-cephem-4-carboxylic acid
7-D-mandelamido-3-(5-N,N-dipropylcarbamoylmethyl-1,2,4-triazol-3-ylthiomethyl)-3-cephem-4-carboxylic acid
7-D-mandelamido-3-(5-N,N-dibutylcarbamoylmethyl-1,2,4-triazol-3-ylthiomethyl)-3-cephem-4-carboxylic acid
7-(D-α-aminophenylacetamido)-3-(5-N,N-diethylcarbamoylmethyl-1,2,4-triazol-3-ylthiomethyl)-3-cephem-4-carboxylic acid
7-(D-α-aminophenylacetamido)-3-(5-N,N-diproplycarbamoylmethyl-1,2,4-triazol-3-ylthiomethyl)-3-cephem-4-carboxylic acid
7-(D-α-aminophenylacetamido)-3-(5-N,N-dibutylcarbamoylmethyl-1,2,4-triazol-3-ylthiomethyl)-3-cephem-4-carboxylic acid
7-(D-α-amino-4-hydroxyphenylacetamido)-3-(5-N,N-diethylcarbamoylmethyl-1,2,4-thiazol-3-ylthiomethyl)-3-cephem-4-carboxylic acid
7-(D-α-amino-4-hydroxyphenylacetamido)-3-(5-N,N-dipropylcarbamoylmethyl-1,2,4-triazol-3-ylthiomethyl)-3-cephem-4-carboxylic acid
7-(D-α-amino-4-hydroxyphenylacetamido)-3-(5-N,N-dibutylcarbamoylmethyl-1,2,4-triazol-3-ylthiomethyl)-3-cephem-4-carboxylic acid.

EXAMPLE 39

An injectable pharmaceutical composition is formed by adding sterile water or sterile saline solution (2 ml.) to 500 mg. of 7-D-mandelamido-3-(5-carboxymethyl-1,2,4-triazol-3-ylthiomethyl)-3-cephem-4-carboxylic acid, sodium salt.

Pharmaceutical compositions of the other antibacterial compounds disclosed above may be formulated in a similar manner.

EXAMPLE 40

A tablet or capsule is formed from 500 mg. of 7-(D-α-amino-4-hydroxyphenylacetamido)-3-(4-carbamoyl-1,2,3-triazol-5-ylthiomethyl)-3-cephem-4-carboxylic acid, 250 mg. of lactose and 75 mg. of magnesium stearate.

Tablets or capsules of the other antibacterial compounds disclosed above may be formulated in a similar manner.

What is claimed is:

1. A pharmaceutical composition having anti-bacterial activity comprising in an effective but nontoxic amount to produce said activity, a compound of the formula:

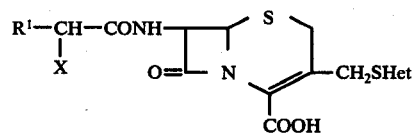

in which:
R¹ is thienyl, phenyl or phenyl substituted with one or two groups selected from hydroxy, halo, nitro, hydroxymethyl, amino, lower alkylamino, di(lower)alkylamino, or carboxymethylamino, each alkyl having from one to four carbon atoms;
X is amino or hydroxy; and
Het is 1,2,4-triazolyl or 1,2,3-triazolyl each of which is substituted with —(CHR²)ₙ COR³ were R² is hydrogen or lower alkyl or from one to four carbon atoms, n is zero to six and R³ is hydroxy, lower alkoxy of from one to four carbon atoms, amino, lower alkylamino or di(lower)alkylamino, each alkyl having from one to four carbon atoms, or a non-toxic pharmaceutically acceptable salt thereof, and a pharmaceutically acceptable carrier therefor.

2. A pharmaceutical composition according to claim 1 comprising 7-mandelamido-3-(5-carboxymethyl-1,2,4-triazol-3-ylthiomethyl)-3-cephem-4-carboxylic acid and a pharmaceutically acceptable carrier therefore.

3. A pharmaceutical composition according to claim 1 comprising 7-(α-amino-4-hydroxyphenylacetamido)-3-(4-carbamoyl-1,2,3-triazol-5-ylthiomethyl)-3-cephem-4-carboxylic acid and a pharmaceutically acceptable carrier therefor.

4. A pharmaceutical composition according to claim 1 comprising 7-mandelamido-3-(4-carboxyl-1,2,3-triazol-5-ylthiomethyl)-3-cephem-4-carboxylic acid and a pharmaceutically acceptable carrier therefor.

5. A pharmaceutical composition according to claim 1 comprising 7-(α-aminophenylacetamido)-3-(4-carboxy-1,2,3-triazol-5-ylthiomethyl)-3-cephem-4-carboxylic acid and a pharmaceutically acceptable carrier therefor.

6. A pharmaceutical composition according to claim 1 comprising 7-(α-aminophenylacetamido)-3-(4-carbethoxy-1,2,3-triazol-5-ylthiomethyl)-3-cephem-4-carboxylic acid and a pharmaceutically acceptable carrier therefor.

7. A pharmaceutical composition according to claim 1 comprising 7-(α-amino-4-hydroxyphenylacetamido)-3-(4-carbethoxy-1,2,3-triazol-5-ylthiomethyl)-3-cephem-4-carboxylic acid and a pharmaceutically acceptable carrier therefor.

8. A pharmaceutical composition according to claim 1 comprising 7(α-aminophenylacetamido)-3-(5-carboxymethyl-1,2,4-triazol-3-ylthiomethyl)-3-cephem-4-carboxylic acid and a pharmaceutically acceptable carrier therefor.

9. A pharmaceutical composition according to claim 1 comprising 7-(α-amino-4-hydroxyphenylacetamido)-3-(5-carboxymethyl-1,2,4-triazol-3-ylthiomethyl)-3-cephem-4-carboxylic acid and a pharmaceutically acceptable carrier therefor.

10. A pharmaceutical composition according to claim 1 comprising 7-(α-aminophenylacetamido)-3-(5-carbethoxymethyl-1,2,4-triazol-3-ylthiomethyl)-3-cephem-4-carboxylic acid and a pharmaceutically acceptable carrier therefor.

11. A method of treating bacterial infections comprising administering internally either orally or by injection to an infected or susceptible warm-blooded animal an antibacterially effective but nontoxic dose of a compound of the formula:

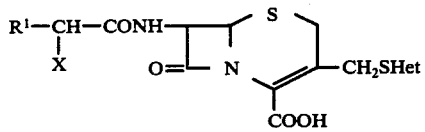

in which:
R$^1$ is thienyl, phenyl or phenyl substituted with one or two groups selected from hydroxy, halo, nitro, hydroxymethyl, amino, lower alkylamino, di(lower)alkylamino, or carboxymethylamino, each alkyl having from one to four carbon atoms;

X is amino or hydroxy; and

Het is 1,2,4-triazolyl or 1,2,3-triazolyl each of which is substituted with —(CHR$^2$)$_n$COR$^3$ where R$^2$ is hydrogen or lower alkyl or from one to four carbon atoms, $n$ is zero to six and R$^3$ is hydroxy, lower alkoxy of from one to four carbon atoms, amino, lower alkylamino or di(lower) alkylamino, each alkyl having from one to four carbon atoms, or a non-toxic pharmaceutically acceptable salt thereof.

12. A method as claimed in claim 11, in which the compound is 7-mandelamide-3-(5-carboxymethyl-1,2,4-triazol-3-ylthiomethyl)-3-cephem-4-carboxylic acid.

13. A method as claimed in claim 11, in which the compound is 7-(α-amino-4-hydroxyphenylacetamido)-3-(4-carbamoyl-1,2,3-triazol-5-ylthiomethyl)-3-cephem-4-carboxylic acid.

14. A method as claimed in claim 11 in which the compound is 7-mandelamido-3-(4-carboxy-1,2,3-triazol-5-ylthiomethyl)-3-cephem-4-carboxylic acid.

15. A method as claimed in claim 11 in which the compound is 7-(α-aminophenylacetamido)-3-(4-carboxy-1,2,3-triazol-5-ylthiomethyl)-3-cephem-4-carboxylic acid.

16. A method as claimed in claim 11 in which the compound is 7-(α-aminophenylacetamido)-3-(4-carbethoxy-1,2,3-triazol-5-ylthiomethyl)-3-cephem-4-carboxylic acid.

17. A method as claimed in claim 11 in which the compound is 7-(α-amino-4-hydroxyphenylacetamido)-3-(4-carbethoxy 1,2,3-triazol-5-ylthiomethyl)-3-cephem-4-carboxylic acid.

18. A method as claimed in claim 11 in which the compound is 7-(α-aminophenylacetamido)-3-(5-carboxymethyl-1,2,4-triazol-3-ylthiomethyl)-3-cephem-4-carboxylic acid.

19. A method as claimed in claim 11 in which the compound is 7-(α-amino-4-hydroxyphenylacetamido)-3-(5-carboxymethyl-1,2,4-triazol-3-ylthiomethyl)-3-cephem-4-carboxylic acid.

20. A method as claimed in claim 11 in which the compound is 7-(α-aminophenylacetamido)-3-(5-carbethoxymethyl-1,2,4-triazol-3-ylthiomethyl)-3-cephem-4-carboxylic acid.

UNITED STATES PATENT AND TRADEMARK OFFICE
CERTIFICATE OF CORRECTION

PATENT NO. : 4,060,610

DATED : November 29, 1977

INVENTOR(S) : David A. Berges

It is certified that error appears in the above-identified patent and that said Letters Patent are hereby corrected as shown below:

Claim 4:

Column 22, line 66 change --(4-carboxyl)-- to "(4-carboxy)"

Claim 12:

Column 24, line 13 change --7-mandelamide-- to "7-mandelamido"

Signed and Sealed this

Second Day of May 1978

[SEAL]

Attest:

RUTH C. MASON
Attesting Officer

LUTRELLE F. PARKER
Acting Commissioner of Patents and Trademarks